United States Patent [19]

Mims

[11] 4,058,555
[45] Nov. 15, 1977

[54] PROCESS FOR THE PURIFICATION OF MIXED ACIDS

[75] Inventor: Samuel S. Mims, Odessa, Tex.

[73] Assignee: El Paso Products Company, Odessa, Tex.

[21] Appl. No.: 843,028

[22] Filed: July 18, 1969

[51] Int. Cl.$^2$ .................. C07C 69/40; C07C 69/42; C07C 69/44

[52] U.S. Cl. .................. 560/191; 260/531 R; 260/533 C; 260/537 R; 260/537 P

[58] Field of Search ............ 260/485 S, 485 R, 533 C, 260/531, 537 O

[56] References Cited

U.S. PATENT DOCUMENTS

| | | | |
|---|---|---|---|
| 2,824,122 | 2/1958 | Kuceski | 260/537 P |
| 2,968,674 | 1/1961 | Franke et al. | 260/485 R |
| 3,329,712 | 7/1967 | Danly et al. | 260/533 C |
| 3,365,490 | 1/1968 | Arthur et al. | 260/531 |

FOREIGN PATENT DOCUMENTS

| | | | |
|---|---|---|---|
| 705,578 | 3/1941 | Germany | 260/484 |
| 933,714 | 8/1963 | United Kingdom | |

*Primary Examiner*—Jane S. Myers
*Attorney, Agent, or Firm*—DePaoli & O'Brien

[57] ABSTRACT

Complex mixtures of polycarboxylic organic acids and their precursors, such as the by-products from the air oxidation of cyclohexane and its derivatives, are treated with nitric acid under hydrolytic conditions, esterified with an alcohol, extracted with an immiscible solvent such as benzene, the extraction preferably being carried out simultaneously with esterification, and separated into component diesters.

8 Claims, 1 Drawing Figure

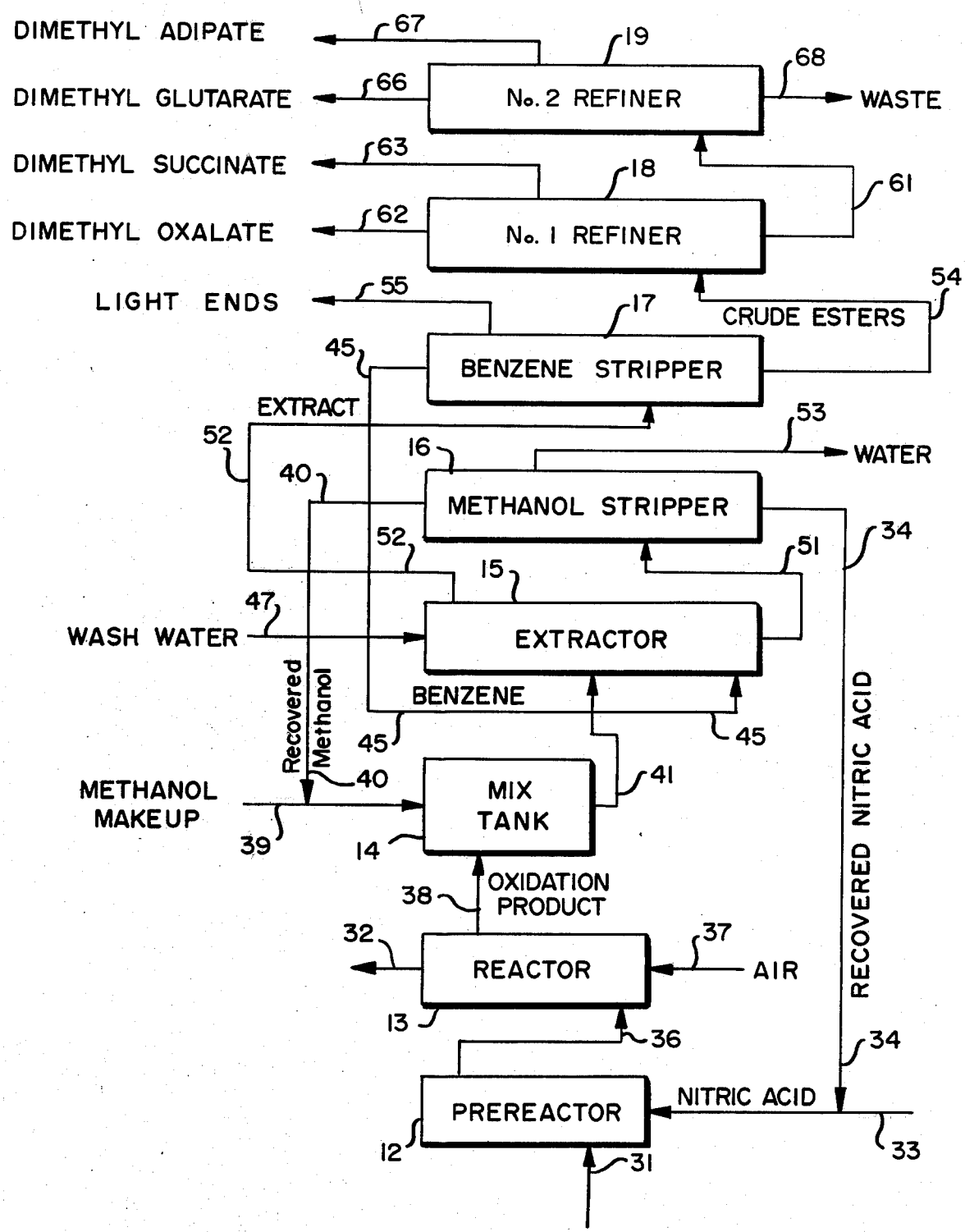

PROCESS FOR THE PURIFICATION OF MIXED ACIDS

BACKGROUND OF THE INVENTION

1. Field of the Invention

This invention relates to a process for forming, recovering and separating organic acids and particularly relates to a process for separating intermixed polycarboxylic acids which are contaminated with catalytic materials, tarry materials, color bodies or degradation products. This invention specifically relates to a process in which the water extractable, nonvolatile by-products from the air oxidation of cyclohexane are subjected to further oxidation under hydrolytic conditions, esterified in an aqueous solution, extracted and separated into component diesters of polycarboxylic acids, whereby the esters or acids are then separately recovered.

2. Description of the Prior Art

Adipic acid, of course, is used in large quantities for the production of nylon by reaction with alkylene diamines to produce polyamides which are capable of being spun into fibers having a number of well known desirable characteristics. As a result there have been developed a number of processes for the preparation of adipic acid. One of the most preferred processes for making adipic acids in commercial quantities is the two-stage oxidation of cyclohexane, the first stage being a partial oxidation step using air or oxygen to produce partially oxidized products comprising primarily cyclohexanol and cyclohexanone, this mixture often being called "anolone," as well as minor amounts of dicarboxylic acids and dicarboxylic acid precursors, and a substantial amount of unreacted cyclohexane which is recycled in a continuous process. In the second stage of this reaction, the cyclohexanol and cyclohexanone, which are contained in an organic phase after separation from an aqueous phase, are oxidized with nitric acid at elevated temperatures to produce a resulting oxidate mixture comprising a major amount of adipic acid and smaller amounts of other materials including other dicarboxylic acids such as glutaric acid and succinic acid as well as catalytic components and spent nitric acid. The art is also well aware of a number of processes for recovery of the desirable adipic acid product as well as the by-product components. The processes, and various improvements thereon, have been disclosed, for example, in U.S. Pat. Nos. 2,439,513; 2,557,282; 2,791,566; 2,840,607; 2,971,010; and 3,338,959.

In this two-stage oxidation process, it has been found that in the first or air-oxidation stage, there is obtained, in addition to the partial oxidation products comprising cyclohexanol and cyclohexanone, a number of by-products which are not ideal for use in the nitric acid oxidation step. Thus, in this air-oxidation reaction, there is obtained an organic phase containing the desired cyclohexanol and cyclohexanone products as well as cyclohexane starting material and an aqueous phase of undesirable by-product materials comprising a small amount of monobasic acids, a larger amount of dibasic acids, such as oxalic acid, succinic acid, glutaric acid and adipic acid, as well as a considerable amount of oxygenated monobasic acids such as ω-hydroxyhexanoic acid and larger amounts of lactones, esters and polymeric esters.

As indicated, a large portion of this aqueous by-product fraction is normally removed from the air oxidation product and the latter, after further purification, is forwarded to the nitric acid oxidation step. A preferred technique for removing a portion of this by-product aqueous fraction from the air oxidation reactor effluent consists essentially of carrying out a water extraction on the reactor effluent or on the reactor effluent from which a portion of the unconverted cyclohexane has been removed. The aqueous phase, after carrying out this extraction, contains a small quantity of cyclohexanol and cyclohexanone and larger amounts of water-soluble and partially water-soluble compounds. Concentration of this aqueous extract by volatilization results in removal of a large portion of the water which can be re-used in the extraction process, and in removal of nearly all of the cyclohexanol and cyclohexanone as well as other volatile compounds. These can then be returned to the purification train of the air oxidation process.

The incorporation of the resulting non-volatile mixture, which, as indicated, contains monobasic and dibasic acids as well as oxygenated monobasic acids, lactones, esters and polymeric esters, directly into the feed of the nitric acid oxidation step of the adipic acid process, will result in an increase in the yield of adipic acid per unit of cyclohexane consumed, but there are practical disadvantages to doing this. Thus, there are inordinate increases in nitric acid consumption, in foaming withing with reaction mixture, in off-gas formation and in production of succinic and glutaric acids. These disadvantages in turn cause a significant reduction in the production capacity of an adipic acid plant of a given size and thus outweigh the increase in adipic acid yield. On the other hand, purification of the adipic acid or other valuable compounds present in the concentrated aqueous solution of extractable nonvolatile by-products is also impractical due to the complex nature of the mixture. Therefore, as a result of the difficulties mentioned, this by-product mixture is ordinarily treated as waste, the disposition of which is in itself an expensive process.

A recent patent, U.S. Pat. No. 3,365,490, is concerned with this problem and discloses a process for the nitric acid oxidation of this by-product material apart from the nitric acid oxidation of the main product resulting from the air-oxidation process and using reaction conditions different from those used in the nitric acid oxidation step. While this prior patent procedure provides increased yields of adipic acid relative to yields of the other dibasic acids, nevertheless, the dibasic acids produced by this process are difficult to separate, both from the reaction mixture and also from each other, due to the presence of relatively large amounts of succinic acid and glutaric acid which are produced in the process. Basically, this patent provides an improvement which comprises concentrating the effluent from the air-oxidizer to about 60–80% cyclohexane, extracting a useful portion of the non-volatile by-products from the organic phase with water, concentrating the aqueous extract and employing the resulting steam to steam-distill the cyclohexanol and cyclohexanone away from the non-useful portion of the non-volatile residue remaining in the organic phase and oxidizing the residue from the aqueous extract to adipic acid with aqueous 30–70% nitric acid at a low temperature (35°–60° C.) in the presence of added $NO_2$. The resultant product is a mixture of the dicarboxylic acids, which, as pointed out above, is still difficult to separate. Quite obviously, therefore, this patent does not provide means by which the other acids present can be recovered and the yield of desirable products maximized.

There are also processes known in the art by which a mixture of dicarboxylic acids can be treated for separation of the acids from each other. Thus, U.S. Pat. No. 2,824,123 describes a process for the separation of dicarboxylic acids by forming the diesters thereof in a conventional manner and distilling the esters by conventional techniques to effect partial separation and cooling the distilled fractions to crystallize esters of the acids. Thus, this patent describes a process for the separation of dicarboxylic acids one from another but not where such acids are contained in an oxidate stream. Similarly, companion U.S. Pat. No. 2,824,122 describes a process for the selective removal of dibasic acids from aqueous streams by converting the acids to ester derivatives with a water-immiscible alcohol and removing the water therefrom during the esterification step. In this latter process an azeotroping agent is often added to the mixture to increase the efficiency of water removal. Neither of these patents however discloses processes by which the polycarboxylic acids resulting from the nitric acid oxidation can be separated from the aqueous stream and from each other so as to recover all desirable and useful products.

It is accordingly clear that a need remains in the art for processes by which valuable products can be effectively recovered from the aqueous by-product extract obtained from the air-oxidation of cyclohexane which can be employed to maximize the production of adipic acid and result in increased efficiency of the overall process.

SUMMARY OF THE INVENTION

It is accordingly one object of this invention to provide a process for isolating organic dibasic acids from an aqueous heterogeneous composition obtained from the air-oxidation of cyclohexane.

A further object of this invention is to provide a process for forming, recovering and isolating difficultly separable organic polycarboxylic acids from a purge stream which has been isolated from the air-oxidation of cyclohexane whereby the acids are converted to esters and the esters are obtained as a mixture or separated from each other.

A still further object of this invention is to provide a process for treating the concentrated aqueous extract of by-products resulting from the air-oxidation of cyclohexane with nitric acid, treating the resulting mixture with a water-miscible alcohol to form the esters of the acids contained therein while simultaneously extracting the esters formed with a water-immiscible solvent and recovering the resulting esters separately or as a mixture therefrom.

Other objects and advantages of the invention will become apparent as the description thereof proceeds.

In satisfaction of the foregoing objects and advantages, the process of this invention provides a procedure for the recovery and isolation of valuable products obtained from the concentrated water extractant solution of by-products of the air-oxidation of cyclohexane, which process comprises treating the aqueous solution with nitric acid to hydrolyze lactones, esters and polymeric esters present and complete the oxidation of oxidizable components, treating the mixture with a water-miscible alcohol to esterify the esters present, treating the esterifying mixture with a water-immiscible solvent, preferably simultaneously, to extract the esters formed from the aqueous mixture, separating the resulting organic and aqueous layers and recovering the esters from the organic extract. The process of this invention also provides a continuous procedure for effecting these separations whereby the oxidizable components are further oxidized to desirable components and the resulting oxidized mixture is treated for formation and separation of the esters, preferably by simultaneous extraction, whereby the esters are removed and separated from each other and the water-immiscible extractant solvent is recovered for re-use in the continuous process.

BRIEF DESCRIPTION OF THE DRAWING

Reference is now made to the drawing accompanying this invention which describes in schematic form a continuous process for carrying out the process of this invention.

DESCRIPTION OF PREFERRED EMBODIMENTS

As indicated above, the process of this invention is concerned with the treatment of a mixture recovered from the air-oxidation of cyclohexane, which oxidation is well-known in the prior art and need not be further described for purposes of illustrating the present invention.

At the conclusion of this air-oxidation step, there is recovered a mixture of the desired partial oxidation products comprising cyclohexanol and cyclohexanone in admixture with unreacted cyclohexane and an aqueous phase of undesired by-products. As indicated above, the preferred technique for removing this by-product fraction from the air-oxidation reactor effluent so as to not feed it directly to the nitric acid oxidation step, is to carry out a water extraction on the reactor effluent or on the reactor effluent from which a portion of the uncovered cyclohexane has been removed. The resulting aqueous phase, after carrying out this extraction, contains a small quantity of cyclohexanol and cyclohexanone and larger amounts of water soluble and partially water soluble compounds. After the extraction the organic phase is further purified to recover the unconverted cyclohexane and to yield a feed containing primarily the cyclohexanol and cyclohexanone. This is then forwarded directly to the nitric acid oxidation step for conversion to adipic acid. Concentration of the aqueous extract by volatilization will result in removal of a large portion of the water which can be re-used in the extraction step and in removal of nearly all the cyclohexanol and cyclohexanone as well as other volatile compounds. These latter materials can then be returned to the purification train of the air oxidation process.

The resulting concentrated aqueous extract by-product solution contains small amounts of monobasic acids, mainly butyric, valeric and caproic acid; larger amounts of dibasic acids, mainly oxalic, succinic, glutaric and adipic acid; considerable amounts of oxygenated monobasic acids, particularly ω-hydroxyhexanoic acid, as well as large amounts of lactones, esters, and polymeric esters. As suggested hereinbefore, incorporation of this mixture directly into the feed of the nitric acid oxidation step of the adipic acid process results in a number of disadvantages.

In the present invention, the concentrated aqueous extract solution of by-products is employed to prepare diesters of the oxalic, succinic, glutaric and adipic acids, either as a mixture or preferably separated from each other, and if desired, the dibasic acids may be recovered from the corresponding diesters by any technique, such as hydrolysis. Thus, the present invention provides a process by which this concentrated aqueous extract solution of by-products is subjected to further and separate treatment to complete the conversion to dibasic acids and to provide an efficient and economical separation of the dibasic acids from the product mixture so obtained in the form of their esters. This separation of the dibasic acids is achieved by treatment with an alcohol to form an esterifying mixture, and in a highly preferred aspect, simultaneously extracting the esters to promote further conversion of diacids to diesters, and thereafter easily separating one from another by conventional distillation procedures.

In the esterifying treatment, the diacid solution may be treated with the alcohol, and then extracted with the water-immiscible solvent. However, as the esterification is an equillibrium reaction, a highly preferred embodiment of the invention is to extract the esters from the mixture with the water-immiscible solvent simultaneously or as they are being esterified as this serves to upset the equilibrium and form more esters which are then simultaneously extracted.

In practicing the process, the concentrated aqueous extract by-product solution of by-products is subjected to nitric acid oxidation under hydrolytic conditions. Thus, in this step, the aqueous extract solution is fed to a reaction vessel, or prereactor, for mixing with aqueous nitric acid at moderate temperatures. The nitric acid is at a concentration of about 30 to 60%, preferably about 40 to 60% strength. Sufficient nitric acid is added to theoretically oxidize all oxidizable components present, with an equal amount by volume usually more than sufficient. In this prereactor the temperature is maintained from about 30° to 60° C. under which conditions some oxidation under hydrolytic conditions takes place and the lactones, esters and polymeric esters present in the mixture are hydrolyzed.

The mixture from this prereactor then enters the primary oxidation reactor where the oxidation is completed at a temperature of 75° to 125° C., preferably 90° to 100° C. In this reactor, air is also preferably added in sufficient quantities to oxidize the by-product nitric oxide formed in the reaction to nitrogen dioxide. The gases from the reactor are then separated from the mixture and vented for conventional recovery or discarded. As a result of the prereaction and oxidation reaction steps, the oxidation product from the reactor comprises an aqueous solution containing unused nitric acid with small amounts of the monobasic acids and large amounts of the dibasic acids.

This reaction product or oxidation product coming from the reactor is then cooled to below about 60° C. and fed to a container for mixing with a water-miscible alcohol. Preferably the alcohol is added in about equal amounts by volume but at least sufficient alcohol should be added to esterify all the organic acids present in the mixing area. Any alcohol may be employed in this step to effect the esterification but preferably there are utilized the lower alkyl alcohols such as those containing from about 1 to 10 carbon atoms and including for example methanol, ethanol, propyl alcohol, isopropyl alcohol, butyl alcohol, s-butyl alcohol and the like. Obviously, polyols could also be employed if they would effect esterification of the mixture. However, the lower alkyl alcohols, and preferably methanol, represent especially preferred alcohols for use in this esterification step because of their low cost, easy reactivity and greater ease of fractionation of esters. Obviously, mixtures of of alcohols may also be used.

After addition of the alcohol the resulting mixture is thoroughly agitated to mix the oxidation product and alcohol streams, preferably at a temperature above room temperature or about 40° to 60° C., preferably 50° C., with an average hold-up time of less than 1 hour. These conditions have been found sufficient to establish an equilibrium between the organic acids, the alcohol and the esters of the organic acids which are formed.

After the reactants have been thoroughly contacted, the resulting homogeneous aqueous solution containing the alcohol is fed to an extractor which may be a single extractor, a series of mixer-settlers, a tower or a column designed for continuous countercurrent or co-current extraction. Obviously, any type of extractor can be used in this step. In the extractor there is provided intimate contact between the aqueous solution and a water-immiscible extractant solvent which is added to the extractor simultaneously with the homogeneous aqueous solution. The water-immiscible extractant solvent which is added can be any solvent which is immiscible with water and which will operate to extract the esters present from the aqueous solution. Suitable immiscible solvents which have been found to be particularly suitable for this aspect of the process include the aromatic hydrocarbons, polarizable materials and polar solvents as opposed to materials which do not show these characteristics. In general aromatic hydrocarbons such as benzene, toluene, xylene, ethylbenzene and the like as well as halogenated aliphatic and aromatic hydrocarbons such as chloroform, chlorbenzene, dichlorbenzene and the like are most suitable. Also in certain instances water-immiscible materials such as pelargonic acids and the like may also be used. In general, however, any material which is substantially water-immiscible and which will extract a good portion of the esters may be employed in this aspect of the process. Of these several extractive solvents, benzene is an especially suitable immiscible solvent as it is readily available, chemically inert, easily recovered and provides good and consistent results.

In the extractor it is necessary that intimate contact between the aqueous and water-immiscible extractive solvent be maintained. Preferably the immiscible solvent is fed to the extractor so as to rise through the aqueous solution as it flows downward so as to provide countercurrent contact in the extractor and therefore effect good contact therebetween. As this occurs the esters of the organic acids in the aqueous solution containing the alcohol transfer into the water-immiscible solvent. Simultaneously, once good contact is established, the equilibrium in the aqueous phase is upset by removal of the esters, thus providing a driving force for formation of more esters as the extraction continues. In this fashion, by continuous reaction, practically all of the acids in the stream leaving the reactor are transformed into esters which leave the extractor in the water-immiscible extractant solution. Therefore, an important aspect of the invention is the simultaneous extraction of the esters as they are formed so that substantially complete conversion to diesters is obtained.

During the extraction process, wash water is preferably fed into the top section of the extractor in order to wash the extract, thereby removing any traces of the alcohol and nitric acid. When a column is employed, this water continues down the column and is ultimately mixed with the aqueous feed solution. The wash water and aqueous alcohol solution, now stripped of the organic acids, leave the extractor and are fed to an alcohol stripper which may be merely a distillation column operated to remove the unreacted alcohol from the aqueous solution. This alcohol is distilled overhead and recycled to the mixing tank. The aqueous solution containing the nitric acid leaves the bottom of this column and is returned to the prereactor for further use in the continuous process. The alcohol stripper may also be operated with a side draw to remove water thereby increasing the concentration of the nitric acid out of the bottom of the column or reactor. If desired, this side draw of water may be used in part as the wash water in the extractor.

The water-immiscible extract containing the esters leaves the extractor and is fed to a water-immiscible stripper. This is preferably a distillation column operated to recover the water-immiscible solvent from the crude diester mixture. The recovered water-immiscible solvent is then preferably fed back to the extractor for further extraction purposes. The water-immiscible stripper is preferably equipped with a side draw for removal of the small amount of any esters of monobasic acids which may be present in the mixture. These products may then be disposed of as desired, such as by distillation to effect separation and recovery based on the difference in boiling points, or they may be hydrolyzed to form the monobasic acids for recovery.

The crude diester fraction, stripped of water-immiscible solvent and the esters of monobasic acids and comprising the diesters of the dibasic acids present, is taken from the water immiscible stripper and fed to a refiner, the refiner being a distillation column operated to distill the lowest boiling diester present, i.e., the diester of oxalic acid. Simultaneously the diester of succinic acid is removed from the side of the column and the heavier esters and impurities are taken out from the refiner and passed to a second refiner which is operated to distill the diester of glutaric acid overhead and the diester of adipic acid as a side draw leaving the heavy ends at the bottom of the second refiner. These heavy ends, although a small fraction of the original feed to the first refiner, contain in addition to tarry high boiling materials, a portion of the monoesters of dibasic acids and some succinic and glutaric anhydrides produced in the purification train. If desired these recoverable materials may be volatilized away from the highly colored tray materials and returned to the alcohol mixing tank for recycle and untimate recovery.

It will be seen from the above that the process provides means by which the diesters of each of the dicarboxylic acids present in the mixture are recovered separated from each other, from the water and nitric acid present and the monoesters of these dibasic acids as well as esters of monobasic acids. If desired these diesters may be further treated as by hydrolysis to recover the dibasic acids per se or the diesters may be used as desired.

It will thus be seen from consideration of the above process that an effective means is provided by which the water extract considered heretofore as waste is effectively treated by a series of operations which provide a maximum utilization of the valuable dibasic acids and dibasic acid precursor components contained in the water extract and thus provide a means by which the two-step adipic acid process described hereinabove gains added efficiency.

Reference is now made to the drawing accompanying this application wherein a specific working embodiment of a continuous process is set forth using methanol as the alcohol and benzene as the extractant. In the drawing it will be seen that a concentrated aqueous solution of a by-product mixture, recovered from the air-oxidation of cyclohexane, is fed through line 31 to prereactor 12 where it is mixed at a low temperature of about 30° C. with aqueous 50% nitric acid entering via line 33. In the prereactor 12, in the presence of the nitric acid and water, the lactones, esters, and polymeric esters hydrolyze, and some oxidation takes place. The mixture from prereactor 12 then enters the reactor 13 where the oxidation is completed at a temperature of about 95° C. Air is also added to the reactor 13 through line 37 in sufficient quantity to oxidize the nitrogen oxide formed in the reaction to nitrogen dioxide. The gases are separated from the reaction mixture and vented through line 32 for conventional recovery or discarded.

The oxidation product from the reactor 13 consists of an aqueous solution containing unused nitric acid; small amounts of the monobasic acids, mainly butyric, valeric, and caproic acids, and large amounts of dibasic acids, oxalic, succinic, glutaric and adipic. This oxidation product, after cooling to 50° C., is fed to a mix tank 14 through line 38 and there is mixed with about an equal volume of methanol, which enters through line 39. The mix tank 14 is designed to thoroughly mix the two streams of methanol and oxidation product, keep the mixture at about 50° C., and provide hold-up time of about 30 minutes. These conditions establish an equilibrium between the organic acids, the methanol, and the methyl esters of the organic acids.

From mix tank 14, the homogeneous aqueous solution containing the methanol esters extractor 15 through line 41. The extractor 15 may be a series of mixer-settlers, a tower or column designed for continuous countercurrent or co-current extraction, or any other type of extractor. The extractor 15 in this embodiment provides countercurrent contact between the aqueous solution and the water-immiscible extractive solvent, which in this case is benzene.

Typically, the extractor 15 is a packed column into which the benzene extracting solvent is fed through line 45 near the bottom and rises through the aqueous solution which flows downward in a countercurrent fashion from an entrance position below the top of the column. As this countercurrent flow occurs, the methyl esters of the organic acids in the aqueous solution containing methanol transfer into the benzene solvent. The equilibrium in the aqueous phase is upset by removal of the methyl esters, thus providing a driving force for formation of more methyl esters. By this solvent-induced shift of the equilibrium through continuous extraction and continuous reaction, practically all of the acids in the aqueous stream leaving the reactor 13 are transformed into methyl esters which are dissolved by the benzene and leave the extractor 15 in the benzene extract through line 52.

In this embodiment, wash water is fed to the top section of extractor 15 during the extraction operation through line 47 in order to wash the benzene extract and thereby remove traces of methanol and nitric acid therefrom. This water extract continues to flow down the column countercurrently to the benzene extract, and is ultimately mixed with the aqueous solution containing methanol as it leaves extractor 15 through line 51.

The wash water and aqueous methanol solution, now stripped of the organic acids, leave the extractor 15 through line 51 and are fed to the methanol stripper 16. Typically, this is a distillation column which is operated to remove the unreacted methanol from the aqueous solution. The methanol is distilled overhead and is recycled to mix tank 14 for further esterification purposes through line 40 via line 39 where it is combined with any make-up of methanol necessary.

During this procedure, the aqueous solution containing the nitric acid leaves the bottom of the methanol stripper 16 and returns to the prereactor 12 for further use with make-up nitric acid through line 34. The methanol stripper 16 is also operated with a side draw 53 to remove the water separately and thereby increase the concentration of the nitric acid leaving the bottom of the column. If desired, this side draw water may be used, in part, as the wash water by conjoining lines 53 and 47.

The benzene extract leaving extractor 15 through line 52 is fed to benzene stripper 17. This stripper is preferably a distillation column which is operated so as to recover the benzene from the crude dimethyl ester mixture. The recovered benzene is removed through line 45 and fed back to extractor 15 for further extraction. The benzene stripper 17 is further equipped with a side draw 55 for removal of the small amount of methyl esters of monobasic acids which are present and considered to be light ends. The crude dimethyl ester fraction, stripped of benzene and the methyl esters of monobasic acids, is removed from the lower portion of the benzene stripper 17 and fed to a Number 1 Refiner 18.

The Number 1 Refiner is a distillation column which is operated to distill dimethyl oxalate overhead through line 62 for storage and/or recovery of oxalic acid and methanol, to produce dimethyl succinate through the side draw 63 for storage and/or recovery of succinic acid and methanol, and to isolate the heavier esters and impurities at the bottom for transmission to the Number 2 Refiner 19 through line 61.

The Number 2 Refiner is operated to distill dimethyl glutarate overhead through line 66 for storage and/or recovery of glutaric acid and methanol, to produce dimethyl adipate through side draw 67 for storage and/or recovery of adipic acid and methanol, and to isolate the heavy ends from the bottom for disposition as waste through line 68. These heavy ends, although a small fraction of the original feed to the Number 1 Refiner, do contain, in addition to tarry materials, a portion of the monomethyl esters of dibasic acids and some succinic and glutaric anhydrides which are formed in the purification train of the invention, herein defined as consisting of the benzene stripper 17, the Number 1 Refiner 18, and Number 2 Refiner 19. If desired, these recoverable materials leaving through line 68 may be volatilized away from the highly colored tarry materials and returned to the mix tank for recycling and ultimate recovery. This optional step is not shown in the drawing.

The following example illustrates a batch method for conducting the process of the invention. In the example, parts are by weight unless otherwise indicated.

EXAMPLE I

A sample of the concentrated water extractable by-products isolated from the reactor effluent of the air oxidation of cyclohexane was obtained from a commercial plant. Analysis of this material is given in Table I.

TABLE I

| Cyclohexane Oxidation By-Product | |
|---|---|
| Water | 23.0% |
| Succinic Acid | 0.4% |
| Glutaric Acid | 1.8% |
| Adipic Acid | 11.4% |
| Hydroxyhexanoic Acid | 5.9% |
| Other | 57.5% |

This material was fed to a stirred, water-jacketed prereactor at a rate of 4.44 grams/minute. Nitric acid (57% strength) was also fed into this prereactor at a rate of 8.19 grams/minute. The prereactor held 600 ml. and was maintained at a temperature of 57° C. Overflow from this prereactor entered the reactor which was a vessel of similar size maintained at 98° C. Off-gas from this setup contained oxides of nitrogen recoverable as nitric acid which were vented in this laboratory experiment. Overflow from the reactor was collected at a rate of 9.32 grams/minute. This material analyzed as shown in Table II.

TABLE II

| Reactor Product | |
|---|---|
| Nitric Acid | 9.7% |
| Adipic Acid | 9.1% |
| Glutaric Acid | 7.6% |
| Succinic Acid | 3.3% |
| Oxalic Acid | 1.2% |

This reactor product was mixed with an equal volume of methanol to yield a homogeneous solution. This solution was then placed in a jacketed feed vessel maintained at 50° C., and from this vessel was pumped into the top of a 25 mm. diameter × 900mm. long jacketed column packed with 4 mm. glass beads. This column was also maintained at 50° C. Benzene was pumped at the same rate into the bottom of this column which was used as a continuous counter-current extractor. Analyses of the benzene extract and the aqueous raffinate are given in Table III.

TABLE III

| Extraction of Dibasic Acids | | |
|---|---|---|
| Extract Composition | | |
| Dimethyl | Oxalate | 0.1% |
| | Succinate | 1.9% |
| | Glutarate | 4.4% |
| | Adipate | 3.8% |
| Monomethyl | Oxalate | 0.1% |
| | Succinate | 0.6% |
| | Glutarate | 0.9% |
| | Adipate | 1.0% |
| Raffinate Composition | | |
| | Oxalic Acid | 0.4% |
| | Succinic Acid | 0.7% |
| | Glutaric Acid | 1.1% |
| | Adipic Acid | 0.6% |

This extract from this step was then distilled at atmospheric pressure to recover the benzene. The residue from this operation was then distilled under vacuum at 50 mm. of mercury using a twenty-plate Oldershaw distillation column to fractionate the dimethyl esters.

The raffinate from the extraction was distilled at atmospheric pressure to recover the excess methanol. The residue from this operation was then distilled under vacuum to remove water and concentrate the nitric acid for reuse in the oxidation reaction.

This invention has been described hereinbefore with particular reference to the preferred embodiments shown as an adjunct to the air-oxidation of cyclohexane in making adipic acid. However, it is to be understood that the invention is not to be limited thereto, as obvious modification thereover will be apparent to those skilled in the art. Thus the boundaries of this invention should be construed as hereinafter defined in the appended claims.

What is claimed is:

1. In a process for the separation and recovery of components contained in the reactor effluent resulting from the air oxidation of cyclohexane, said reactor effluent comprising cyclohexanol, cyclohexanone, unreacted cyclohexane, monobasic aliphatic organic acids, dibasic aliphatic organic acids, oxygenated monobasic aliphatic organic acids, lactones, esters and polymeric esters; the improved steps comprising:
   a. extracting said reactor effluent with water and permitting layer separation to form, (1) an organic phase containing a major amount of the cyclohexane, cyclohexanol and cyclohexanone, and (2), an aqueous phase containing the organic acids, lactones, esters and polymeric esters and minor amounts of cyclohexane, cyclohexanol and cyclohexanone;
   b. withdrawing said aqueous phase and concentrating to remove the volatile components and provide an aqueous phase concentrate;
   c. mixing said aqueous phase concentrate with about 30–60% aqueous nitric acid at a temperature of about 30° to 60° C. to initiate oxidation and hydrolyze any hydrolyzable materials present and provide an aqueous concentrate/nitric acid resulting mixture;
   d. reacting the aqueous phase concentrate/nitric acid resulting mixture at a temperature of about 75° to 125° C. to oxidize the remaining oxidizable components present;
   e. contacting the resulting mixture in cooled condition with a substantially water-miscible lower alkyl alcohol to form an alcoholic mixture in which esters are formed of the aliphatic organic acids present;
   f. simultaneously contacting said alcoholic mixture with a water-immiscible extractant organic solvent under conditions of intimate contact to extract the esters formed into an organic phase with the extractant solvent and form an organic phase and an aqueous phase; said organic solvent comprising an aromatic hydrocarbon, a halogenated aliphatic hydrocarbon, a halogenated aromatic hydrocarbon or mixture thereof;
   g. withdrawing and separating said organic phase and said aqueous phase;
   h. stripping said aqueous phase to remove any alcohol present, and
   i. distilling said organic phase to recover the alkyl esters.

2. A process according to claim 1 wherein at least a portion of the cyclohexane is removed prior to the water extraction step (a).

3. A process according to claim 2 wherein said aqueous nitric acid is about 40 to 60% strength, is employed in an equal amount by volume based on the volume of the liquid being treated and the oxidizing step with nitric acid is carried out at a temperature of about 90° to 100° C.

4. A process according to claim 3 wherein sufficient air is introduced into the nitric acid oxidizing mixture to oxidize nitric oxides to nitrogen dioxide during the oxidizing step.

5. In a continuous process for the separation and recovery of components contained in the reactor effluent resulting from the air oxidation of cyclohexane, which reaction mixture comprises cyclohexanol, cyclohexanone, unreacted cyclohexane, monobasic aliphatic organic acids, dibasic aliphatic organic acids, oxygenated monobasic aliphatic organic acids, lactones, esters and polymeric esters, the improved steps which comprise:
   a. extracting said reactor effluent with water and permitting layer separation to form; (1), an organic phase containing a major amount of the cyclohexane, cyclohexanol and cyclohexanone, and (2), an aqueous phase containing the aliphatic organic acids, lactones, esters and polymeric esters and minor amounts of the cyclohexane, cyclohexanol and cyclohexanone;
   b. withdrawing said aqueous phase and concentrating to remove a portion of the water, which is recycled to extraction step (a) and most of the cyclohexane, cyclohexanol, cyclohexanone and other volatile components, which are recycled to the organic phase, to provide an aqueous phase concentrate;
   c. mixing said aqueous phase concentrate with about 30–60% aqueous nitric acid at a temperature of about 30° to 60° C. to initiate oxidation and hydrolyze any hydrolyzable materials present and provide an aqueous phase concentrate/nitric acid resulting mixture;
   d. reacting said aqueous phase concentrate/nitric acid resulting mixture at a temperature of about 75° to 125° C. to oxidize the remaining oxidizable components present;
   e. contacting the resulting mixture in cooled condition with a substantially water-miscible lower alkyl alcohol to form an alcoholic mixture in which esters are formed of the aliphatic organic acids present;
   f. simultaneously with esterification step (e), contacting the alcoholic mixture in a countercurrent manner with a water-immiscible extractant organic solvent under conditions of intimate contact to extract the esters substantially as they are formed into the extractant solvent and form an organic phase and an aqueous phase, said extractant organic solvent comprising an aromatic hydrocarbon, a halogenated aliphatic hydrocarbon, a halogenated aromatic hydrocarbon or mixture thereof;
   g. separating said organic phase and said aqueous phase;
   h. stripping said aqueous phase to recover (1) any excess alcohol which is recycled to the esterification step, and (2) an aqueous nitric acid mixture which, after adjustment of concentration, is recycled to the nitric acid oxidation step; and
   i. withdrawing the organic phase and distilling to recover the extractant solvent which is recycled to the extraction step, and recovering the esters.

6. A continuous process according to claim 5 wherein said aqueous nitric acid in the oxidation step is about 40 to 60% strength, is employed in an equal amount by volume, the oxidizing step with nitric acid is carried out at a temperature of about 90° to 100° C., and the oxidizing step is carried out in the presence of a stream of air.

7. A continuous process according to claim 6 characterized in that the esterifying alcohol is used in amount of about equal volume and contact with the aqueous solution is carried out at a temperature of about 40° to 60° C. for a contact period of less than 1 hour.

8. A continuous process according to claim 7 wherein the alcohol is methyl alcohol, the extractant solvent is benzene and the resulting organic phase is distilled with fractionation to provide the methyl esters of the organic acids present.

* * * * *